United States Patent
Lee et al.

(10) Patent No.: US 8,301,215 B2
(45) Date of Patent: Oct. 30, 2012

(54) BIOSIGNAL MEASUREMENT APPARATUS

(75) Inventors: Jong Youn Lee, Yongin-si (KR); Kenichi Yamakoshi, Ishikawa (JP); Kun Soo Shin, Seongnam-si (KR); Hye Jin Jung, Seoul (KR); Shinobu Tanaka, Kanazawa (JP); Takehiro Yamakoshi, Kanazawa (JP)

(73) Assignees: Samsung Electronics Co., Ltd., Suwon-Si (KR); National University Corporation Kanazawa University, Ishikawa (JP)

( * ) Notice: Subject to any disclaimer, the term of this patent is extended or adjusted under 35 U.S.C. 154(b) by 1523 days.

(21) Appl. No.: 11/819,923

(22) Filed: Jun. 29, 2007

(65) Prior Publication Data
US 2008/0058623 A1 Mar. 6, 2008

(30) Foreign Application Priority Data
Jun. 30, 2006 (KR) .................. 10-2006-0061157

(51) Int. Cl.
*A61B 5/1455* (2006.01)
*A61B 5/02* (2006.01)

(52) U.S. Cl. ........ 600/324; 600/323; 600/340; 600/503; 600/506

(58) Field of Classification Search .................. 600/310, 600/322–32, 340, 344, 473, 476, 481, 500–503, 600/322–324, 506
See application file for complete search history.

(56) References Cited

U.S. PATENT DOCUMENTS

| | | | |
|---|---|---|---|
| 4,859,057 A * | 8/1989 | Taylor et al. .................. 600/323 |
| 5,099,853 A | 3/1992 | Uemura et al. | |
| 5,131,400 A * | 7/1992 | Harada et al. .................. 600/500 |
| 5,176,143 A * | 1/1993 | Eckerle et al. .................. 600/490 |
| 5,238,000 A * | 8/1993 | Niwa .......................... 600/502 |
| 5,771,001 A * | 6/1998 | Cobb .......................... 340/573.1 |
| 5,904,654 A * | 5/1999 | Wohltmann et al. .......... 600/481 |
| 6,334,850 B1 | 1/2002 | Amano et al. | |
| 6,491,647 B1 | 12/2002 | Bridger et al. | |
| 6,529,754 B2 | 3/2003 | Kondo | |
| 2002/0095092 A1 | 7/2002 | Kondo et al. | |

FOREIGN PATENT DOCUMENTS

| | | |
|---|---|---|
| JP | 2004-129979 | 4/2004 |
| JP | 2005-246090 | 9/2005 |
| KR | 20-0380928 | 3/2005 |

OTHER PUBLICATIONS

Japanese Notice of Rejection issued Sep. 21, 2010 in corresponding Japanese Patent Application 2007172222.

* cited by examiner

*Primary Examiner* — Eric Winakur
*Assistant Examiner* — Chu Chuan (JJ) Liu
(74) *Attorney, Agent, or Firm* — Staas & Halsey LLP

(57) ABSTRACT

A biosignal measurement apparatus including: a bracelet membrane to wear around a user's wrist; a fixing supporter to install in a first side portion of the bracelet membrane and to support a first side portion of the wrist; a moving supporter to install in a second side portion of the bracelet membrane, to move towards the fixing supporter, and closely to attach to a second side portion of the wrist; and an information control unit to calculate a distance between the first side portion of the wrist and the second side portion of the wrist by detecting a movement distance of the moving supporter, and to calculate a displacement of the radial artery of the wrist by using a predetermined constant and the calculated distance between the first side portion of the wrist and the second side portion of the wrist.

16 Claims, 5 Drawing Sheets

|  | N | MEAN | STANDARD DEVIATION |
|---|---|---|---|
| I1/L1 MALE | 57 | 0.1719 | 0.0402 |
| I1/L1 FEMALE | 21 | 0.1492 | 0.0454 |

FIG. 4

| I1(cm) | I2(cm) | I3(cm) | L1(cm) | L2(cm) | L3(cm) | RATIO(I1/L1) | RATIO(I2/L2) | RATIO(I3/L3) | I1_1 |
|---|---|---|---|---|---|---|---|---|---|
| 1 | 1.5 | 1.3 | 6.3 | 6.9 | 6.8 | 0.159 | 0.217 | 0.191176 | 1.0017 |
| 0.7 | 1.1 | 1 | 6.1 | 6.6 | 6.5 | 0.115 | 0.167 | 0.153846 | 0.7015 |
| 0.9 | 1.2 | 1.4 | 6.3 | 6.5 | 6.6 | 0.143 | 0.185 | 0.212121 | 0.9009 |
| 0.8 | 1.6 | 1.4 | 6.3 | 7.3 | 7.4 | 0.127 | 0.219 | 0.189189 | 0.8001 |
| 1.2 | 1 | 1.2 | 6.4 | 6.1 | 6.4 | 0.188 | 0.164 | 0.1875 | 1.2032 |
| 1.5 | 1.6 | 1.7 | 6.7 | 7 | 7.2 | 0.224 | 0.229 | 0.236111 | 1.5008 |
| 0.9 | 1.4 | 2 | 6.4 | 6.7 | 7.2 | 0.141 | 0.209 | 0.277778 | 0.9024 |
| 1.5 | 1.3 | 1.3 | 6.9 | 6.5 | 6.2 | 0.217 | 0.2 | 0.209677 | 1.4973 |
| 0.8 | 0.8 | 0.9 | 6 | 5.9 | 6.1 | 0.133 | 0.136 | 0.147541 | 0.798 |

FIG. 5

BIOSIGNAL MEASUREMENT APPARATUS

CROSS-REFERENCE TO RELATED APPLICATION

This application claims the benefit of Korean Patent Application No. 10-2006-0061157, filed on Jun. 30, 2006, in the Korean Intellectual Property Office, the disclosure of which is incorporated herein by reference.

BACKGROUND

1. Field

Embodiments relate to a biosignal measurement apparatus, and more particularly, to a biosignal measurement apparatus which can trace a location of a radial artery in a user's wrist by measuring a width of the user's wrist, and measure the user's biosignals from the radial artery, and thereby enables the user to easily and readily measure biosignals irrespective of the user's age, sex, weight, the width of the wrist, and the like.

2. Description of the Related Art

Ubiquitous-related technology may be applied to myriad field in human life. In particular, Ubiquitous-HealthCare (hereinafter, U-HealthCare) has recently been in the spotlight as a notable technology area due to the "well-being" boom. U-HealthCare means Ubiquitous technology which enables anyone to readily receive medical services at any time and at any place by installing medical service-related chips or sensors in places of the user's living space. With U-HealthCare, various types of medical attentions, such as physical examinations, disease management, emergency care, consultation with a doctor and the like, which currently are only performed in hospitals, may be naturally integrated into our daily lives, thus may be accomplished without going to a hospital.

For example, a diabetic may wear a belt having a blood-sugar management system for blood-sugar management. A blood-sugar sensor attached to the belt may check the blood-sugar of the diabetic upon a specified occasion, and calculate the amount of required insulin corresponding thereto. When the blood-sugar of the diabetic becomes drastically low or high, the belt may provide the blood-sugar information to his/her attending physician using a wireless network, and the attending physician who has received the blood-sugar information may write out an optimal prescription or take the optimal action for the medical emergency.

An example of U-HealthCare includes a portable pulse waveform measuring device which enables a user to easily measure the user's pulse waveforms. The portable pulse waveform measuring device is generally configured in the form of a wristwatch or a bracelet. Accordingly, a user may easily measure the user's pulse waveforms by wearing the portable pulse waveform measuring device around a wrist.

When measuring a pulse waveform, the pulse waveform may be obtained from a radial arterial pulse waveform which is sensed from the wrist of the user. Accordingly, to accurately measure pulse waveforms, an exact location of a radial artery of the wrist must be verified. However, since every user has a different size of the wrist, the location of the radial artery of the wrist is different for each user.

Accordingly, in a conventional art, to verify the location of the radial artery which is different for each user, the user is required to directly move a sensor to the location of the radial artery of the user. Also, the user is required to initially measure pulse waveforms at a plurality of locations, and select a location where a most accurate signal may be measured, as the radial artery. Accordingly, the user may suffer inconveniences and introduce inaccuracies.

Accordingly, a biosignal measurement device which can accurately trace a location of a radial artery in the wrist of a user irrespective of the user's age, sex, the size of the wrist, weight, and the like, and thereby can accurately measure the user's biosignals from the radial artery is acutely required.

SUMMARY

Additional aspects and/or advantages will be set forth in part in the description which follows and, in part, will be apparent from the description, or may be learned by practice of the invention.

An aspect of the present invention provides a biosignal measurement device which enables a user to easily and readily measure the user's biosignals irrespective of the user's physical characteristics by accurately tracing a location of a radial artery of the user's wrist according to a value which is obtained by multiplying a width of the wrist and a predetermined constant, and measuring the user's biosignals from the radial artery.

An aspect of the present invention also provides a biosignal measurement apparatus which can measure a user's pulse waveforms by including at least one optical sensor, at least one luminous element, which has two light sources, to emit a red light and an infrared ray respectively, and at least one pressure sensor with respect to a sensor unit for measuring the user's biosignals from a radial artery, and also can measure an oxygen saturation level according to a light absorption difference between the user's oxyhemoglobin and reduced hemoglobin, and can measure a pressure of the radial artery using the pressure sensor, and thereby enables the user to measure the user's blood pressure.

According to an aspect of the present invention, there is provided a biosignal measurement device including: a bracelet membrane to wear around a user's wrist; a fixing support to install in a first side portion of the bracelet membrane and supporting a first side portion of the wrist; a moving support to install in a second side portion of the bracelet membrane, to move towards the fixing support, and closely attaching to a second side portion of the wrist; and an information control unit to calculate a distance between the first side portion of the wrist and the second side portion of the wrist by detecting a movement distance of the moving support, and calculating a displacement of the radial artery of the wrist by using a predetermined constant and the calculated distance between the first side portion of the wrist and the second side portion of the wrist.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF THE EMBODIMENTS

Reference will now be made in detail to the embodiments, examples of which are illustrated in the accompanying drawings, wherein like reference numerals refer to the like elements throughout. The embodiments are described below to explain the present invention by referring to the figures.

Reference will now be made in detail to exemplary embodiments of the present invention, examples of which are illustrated in the accompanying drawings, wherein like reference numerals refer to the like elements throughout. The exemplary embodiments are described below in order to explain the present invention by referring to the figures.

A pulse waveform referred to in the present specification mainly designates a waveform according to the change of the pressure and volume of a blood vascular system and a heart chamber on the basis of a physical change of the heart. A biosignal measurement device according to the present invention can measure a radial arterial pulse waveform from the wrist of the user. The biosignal measurement device may be configured into an element of an accessory which is wearable around the wrist, such as a wristwatch, a bracelet, and the like. Also, the biosignal measurement device may be configured into a unit article such as a bracelet. In the present specification, when the biosignal measurement device is configured into the form of a bracelet will be described.

Hereinafter, exemplary embodiments of the present invention will be described in detail with reference to the accompanying drawings.

Figure 1:
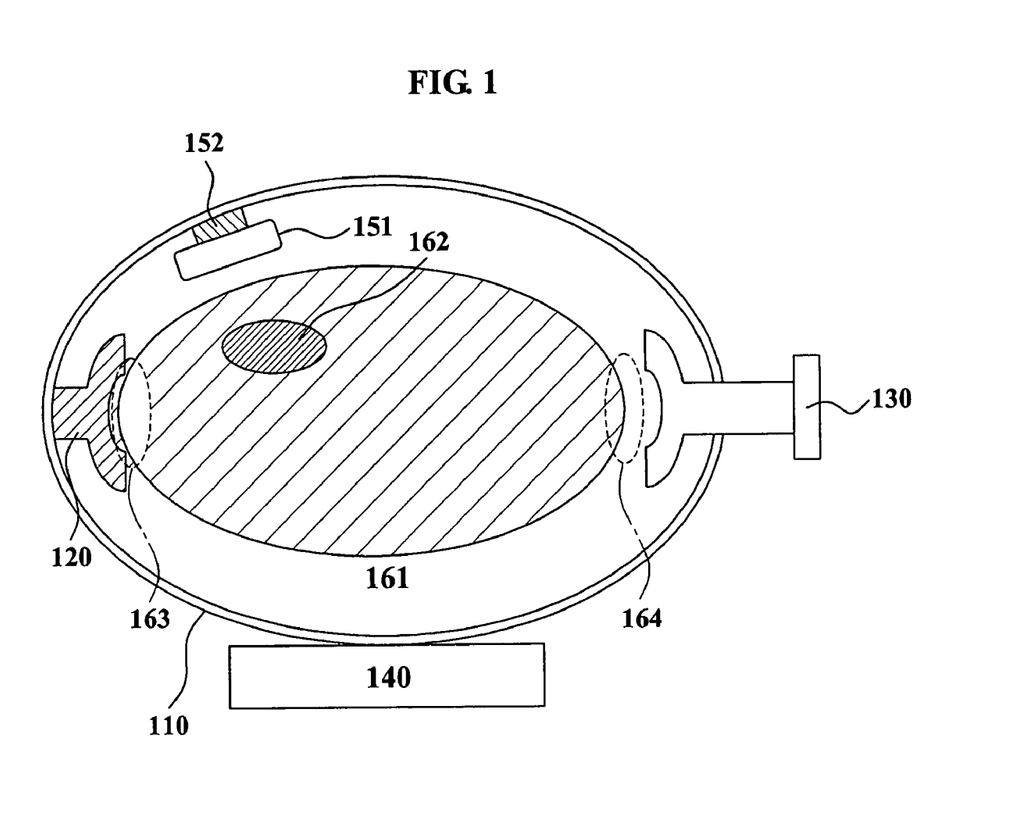
FIG. 1 is a diagram illustrating a shape and configuration of a biosignal measurement apparatus according to an exemplary embodiment of the present invention.

FIG. 1 is a diagram illustrating a shape and configuration of a biosignal measurement device according to an exemplary embodiment of the present invention.

The biosignal measurement device according to the present exemplary embodiment includes a bracelet membrane 110, a fixing support 120, a moving support 130, an information control unit 140, a sensor unit 151, and a sensor actuator 152.

The bracelet membrane 110 may be configured into a shape of a bracelet which is wearable around a wrist 161 of a user. The size of the bracelet membrane 110 may be configured into a size that can be wearable around an adult's wrist.

The fixing supporter 120 is provided in a first side portion of the bracelet membrane 110, and supports a first side portion 163 of the wrist 161. Specifically, when the user wears the bracelet membrane 110 around the wrist 161, the fixing support 120 may contact with or closely attach to the first side portion 163 of the wrist 161 and thereby, support the wrist 161. As an example, when the user wears the wrist membrane 110 around the left wrist, the fixing support 120 may contact with or closely attach to a left side end of the left wrist.

The moving supporter 130 is provided in a second side portion of the bracelet membrane 110, moves towards the fixing supporter 120, and closely attaches to a second side portion 164 of the wrist 161. Specifically, when the user wears the bracelet membrane 110 around the wrist 161, the fixing supporter 120 may contact with or closely attach to the first side portion 163 of the wrist 161 and thereby, support the wrist 161. Also, the moving supporter 130 may be spaced apart from the second side portion 164 of the wrist 161 by a predetermined distance, as shown in FIG. 1.

In this case, the moving supporter 130 may move towards the fixing supporter 120, closely attach to the second side portion 164 of the wrist 161, and thereby support the wrist 161. Specifically, as the moving supporter 130 moves towards the second side portion 164 and thereby closely attaches to the second side portion 164, each of the fixing supporter 120 and the moving support 130 may closely attach to the wrist 161 and support the wrist 161.

The moving supporter 130 may be directly moved by the user actuating the moving supporter 130. Also, like a general sphygmomanometer, the moment the user wears the bracelet membrane 110 around the wrist 161 of the user, the moving supporter 130 may be configured to automatically move towards the second side portion 164 of the wrist 161 and closely attach to the second side portion 164 of the wrist 161.

A method of using an elastic motion, such as a spring, and the like, and a method of using a rotational motion, such as a bolt element, and the like, may be utilized for moving the moving supporter 130.

Initially, when using the elastic motion, the moving supporter 130 may include a predetermined elastic element, such as a spring and the like. The moving supporter 130 may closely attach to the second side portion 164 of the wrist 161 according to an elastic motion of the elastic element. As an example, the moment the user presses the moving supporter 130, the moving supporter 130 may closely attach to the second side portion 164 according to a contracting motion of the elastic element.

When using the rotational motion, the moving supporter 130 may include a predetermined bolt element (not shown). The moving supporter 130 may closely attach to the second side portion 164 of the wrist 161 according to the rotational motion of the bolt element. As an example, when the user rotates the bolt element, the moving supporter 130 may move towards the fixing supporter 120 and closely attach to the second side portion 164 of the wrist 161 as the bolt element rotates.

The information control unit 140 detects a movement distance of the moving supporter 130, and calculates a distance between the first side portion 163 and the second side portion 164 of the wrist 161. Specifically, the information control unit 140 may calculate a width of the wrist 161 by detecting the movement distance of the moving supporter 130.

The information control unit 140 may calculate the width of the wrist 161 by subtracting the movement distance of the moving supporter 130 from a distance between the fixing supporter 120 and the moving supporter 130 before the moving supporter 130 moves.

When the moving supporter 130 includes the elastic element, the information control unit 140 may calculate the movement distance of the moving supporter 130 by using a movement displacement of the elastic element so as to closely attach to the second side portion 164 of the wrist 161.

Also, when the moving supporter 130 includes the bolt element, the information control unit 140 may calculate the movement distance of the moving supporter 130 by using a number of rotations of the bolt element, so as to closely attach to the second side portion 164 of the wrist 161.

As described above, when the distance between the first side portion 163 and the second side portion 164 of the wrist 161, which is the width of the wrist 161, is calculated by detecting the movement distance of the moving supporter 130, the information control unit 140 calculates a displacement of a radial artery of the wrist 161 by using the calculated width of the wrist 161 and a predetermined constant.

The predetermined constant may be set to have a value of 0.1719 or 0.1492. According to an exemplary embodiment of the present invention, the information control unit 140 may calculate the displacement of the radial artery of the wrist 161 by multiplying the predetermined constant and the calculated distance between the first side portion 163 and the second side portion 164. The displacement of the radial may be determined by a distance from the first side portion 163 of the wrist 161.

The predetermined constant may be selected from a predetermined test. Hereinafter, a principle of calculating the constant according to the test will be described with reference to FIGS. 2A through 4.

Figure 2A:
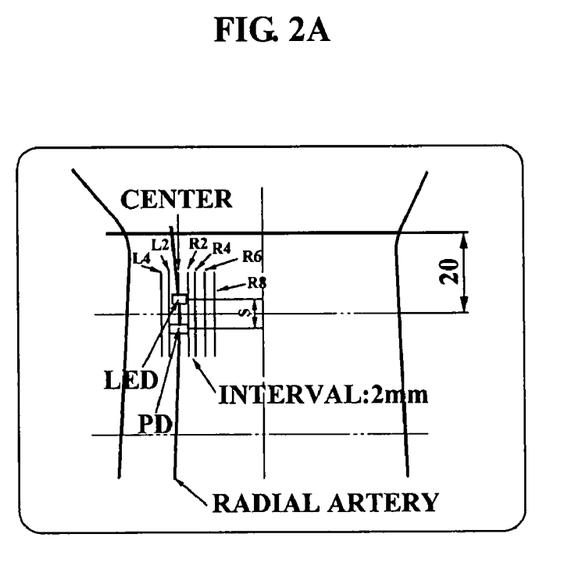
FIGS. 2A and 2B are graphs illustrating test results of the strength of pulse waveforms which are measured using a sensor at a plurality of locations separated from a radial artery of the wrist by various distances, so as to calculate a constant according to an exemplary embodiment of the present invention.
Figure 2B:
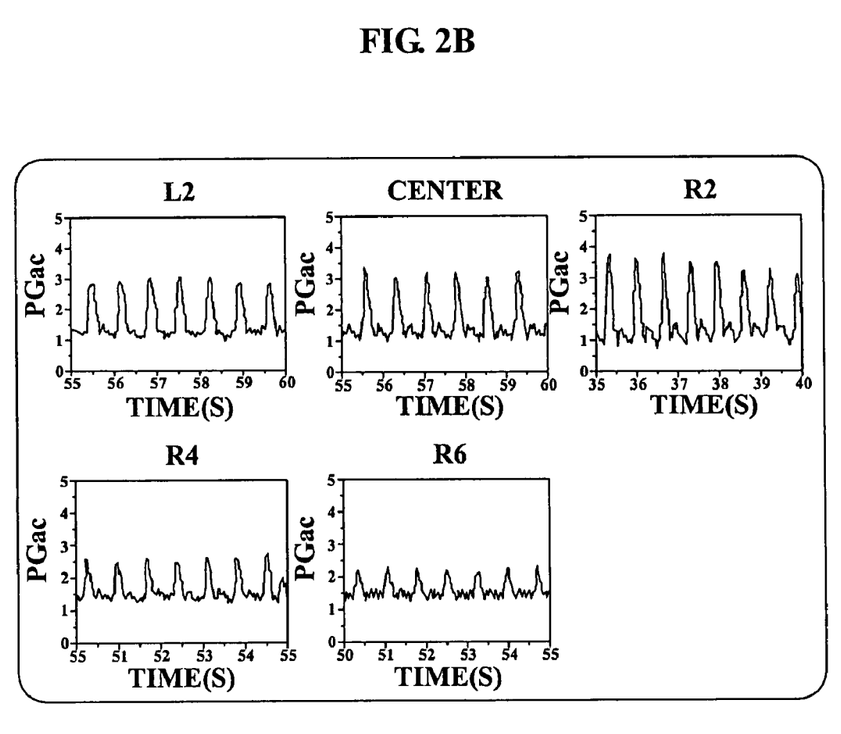

FIGS. 2A and 2B, are graphs illustrating test results of the strength of pulse waveforms which are measured using a sensor(not shown) at a plurality of locations separated from a radial artery of the wrist by various distances to calculate a constant according to an exemplary embodiment of the present invention.

To compare the strength of a pulse waveform signal according to each measurement location of the radial artery, when measuring pulse waveforms at the measurement locations, which are separated towards left and right sides from a center of the radial artery by 2 mm, as shown in FIG. 2A, the graphs as shown in FIG. 2B may be acquired as results.

According to the test results, the pulse waveforms, which were measured at the center of the radial artery and a location R2 corresponding to a location which is separated from the radial artery to the right side by 2 mm, have the greatest amplitudes. Also, the further the location is separated from the center of the radial artery, the smaller a pulse waveform signal becomes. The test results are not symmetrical around the center of the radial artery. Thus, according to the test results, when the sensor is located within 2 mm to the left side and 6 mm to the right side based on the center of the radial artery, pulse waveform signals may be more accurately measured.

Figure 3A:
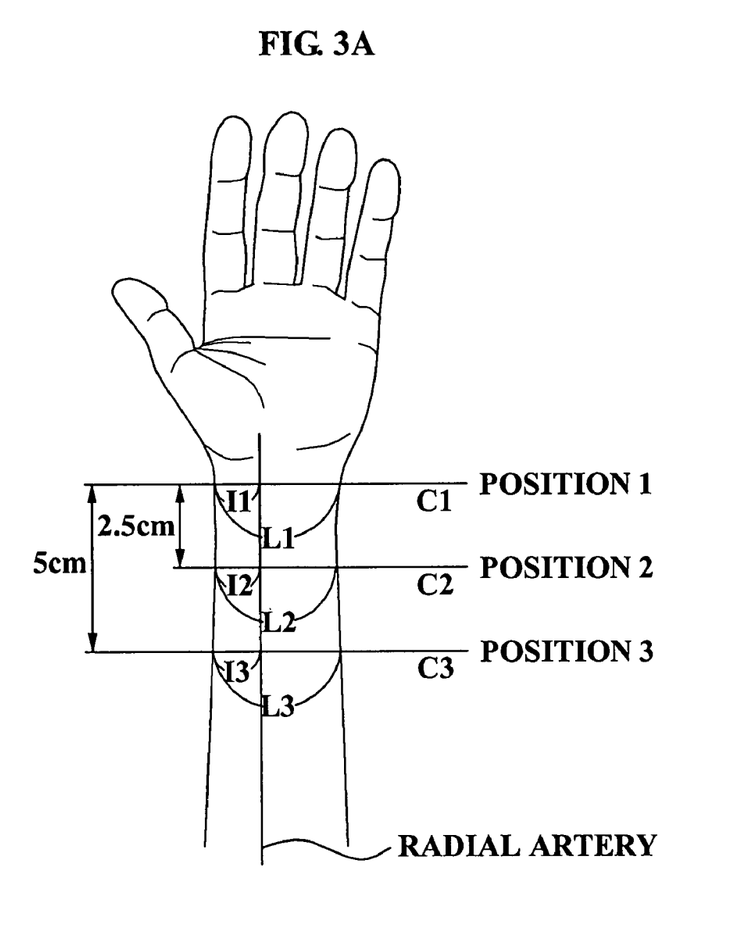
FIGS. 3A and 3B illustrate a reference protocol of a test to measure a location of a radial artery and a table of showing a ratio of a displacement of the radial artery to a width of the wrist according to the test, according to an exemplary embodiment of the present invention.
Figure 3B:
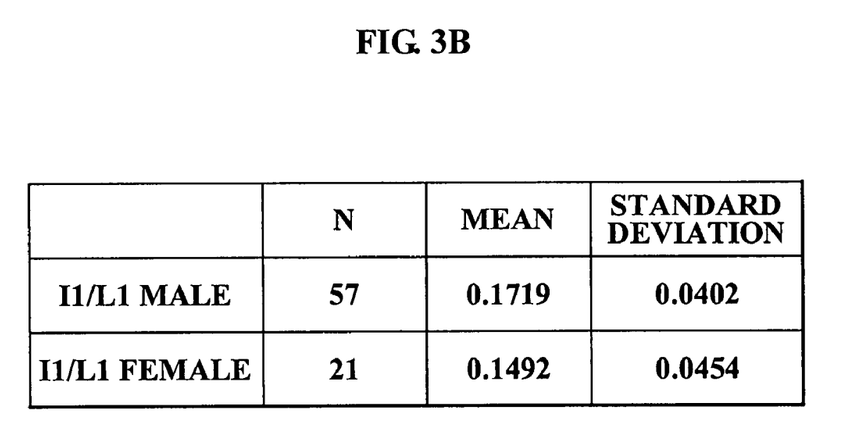

FIGS. 3A and 3B, illustrate a reference protocol of a test for measuring a location of a radial artery and a table of showing a ratio of a displacement of the radial artery to a width of the wrist according to the test, according to an exemplary embodiment of the present invention.

To calculate the constant, a test for measuring a location of an artery from each of 87 test subjects to more quantitatively trace the location of the radial artery was conducted. The test subjects included 19 Korean males and 15 Korean females, 38 Japanese males and 6 Japanese females, and 5 Chinese males and 4 Chinese females.

As shown in FIG. 3A, a most upper portion of skin wrinkles of an anterior surface of the wrist is set as a position 1, and locations, which are separated from the position 1 by 2.5 cm and 5 cm respectively, are set as a position 2 and a position 3. Also, C1 designates the circumference of the wrist in the position 1, C2 designates the circumference of the wrist in the position 2, and C3 designates the circumference of the wrist in the position 3.

Also, I1 designates a distance from a left side end of the wrist to the radial artery in the position 1, I2 designates a distance from the left side end of the wrist to the radial artery in the position 2, and I3 designates a distance from the left side end of the wrist to the radial artery. Tests of calculating the ratio, I1/L1, I2/L2, and I3/L3, of the width, L1, L2, and L3, of the wrist in each of the positions 1, 2, and 3, to the distance, I1, I2, and I3, between the left side end of the wrist and the radial artery were performed.

Also, as a result of calculating a correlation between the ratio, I1/L1, I2/L2, and I3/L3, of the width of the wrist in each of the positions 1, 2, and 3, to the distance between the left side end of the wrist and the radial artery, and the circumference of the wrist, C1, C2, and C3, a correlation coefficient was calculated as −0.359, which proved that the correlation between the width of the wrist and the circumference of the wrist is very low. Accordingly, the circumference of the wrist and the position of the radial artery from the width of the wrist may have almost no relation to each other.

Also, as a result of calculating the ratio, I1/L1, I2/L2, and I3/L3, of the wrist to the distance between the left side end of the wrist and the radial artery according to natural physical tendencies of test subjects with a different sex, a different age, a different weight, and the like, result values as shown in FIG. 3B were obtained. Specifically, as a result of comparing the width of the wrist and the ratio, for example, I1/L1, between the left side end and the radial artery according to a sex, the mean of the males was calculated as 0.17±0.04, and the mean of the females was calculated as 0.15±0.04. Specifically, a p-value was outputted as 0.053, which implies that there is no significant difference according to the sex.

Accordingly, an error was calculated through a process below, to induce a location of the radial artery by using the ratio of the distance between the left side end of the left wrist and the radial artery, and the width of the wrist, which is unaffected by the circumference of the wrist and the sex, the process including: 1) calculating the mean of the ratio, for example, I1/L1, of the width of the wrist to the distance between the left side end of the left wrist and the radial artery, from data which was measured from 87 test subjects; 2) calculating an estimation value of the distance, for example, I1__1, between the left side end of the left wrist and the radial artery by multiplying the mean and the width, for example, L1, of the wrist of each test subject; and 3) acquiring a difference between the estimation value, which is calculated in the above 2), and the actual distance from the left side end of the left wrist to the radial artery.

Figure 4:
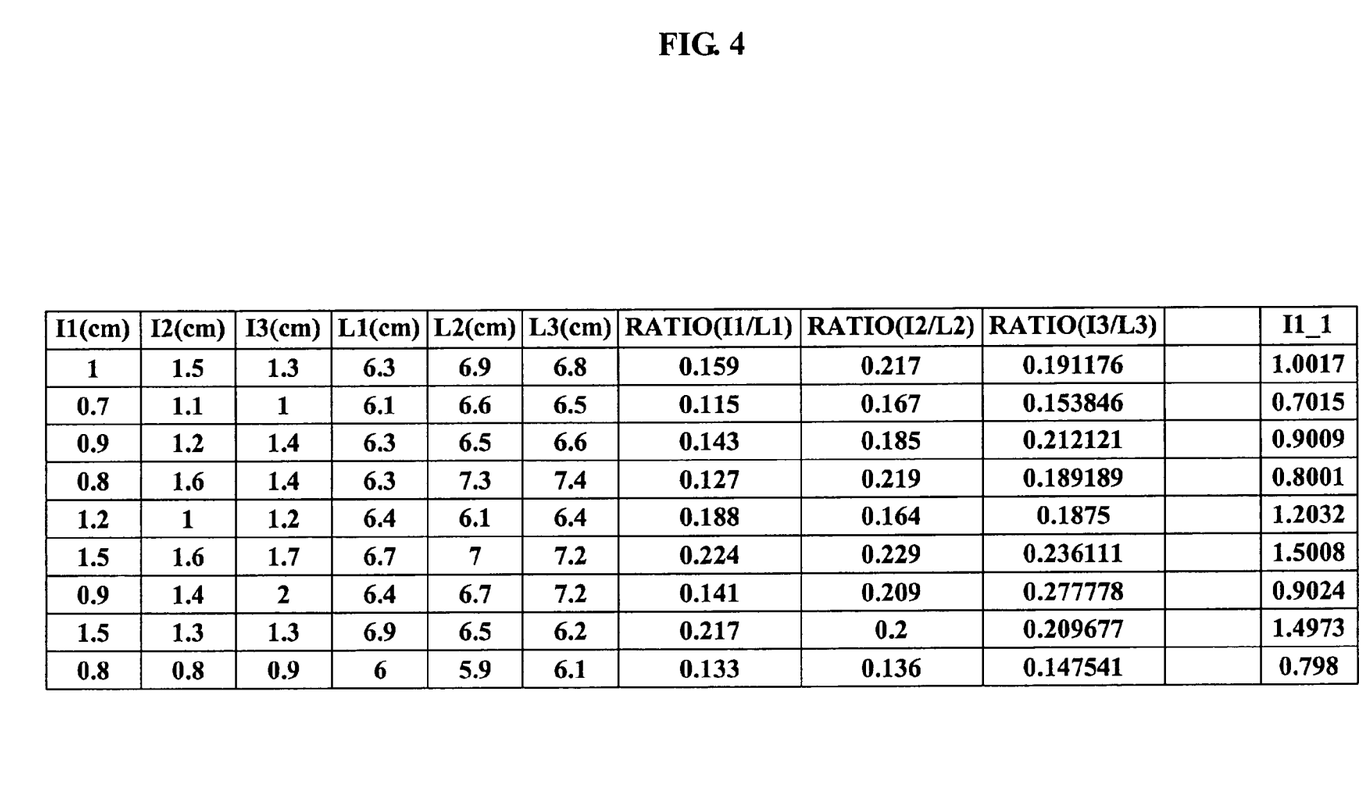
FIG. 4 is a table illustrating a test result value according to an exemplary embodiment of the present invention.

FIG. 4 is a table illustrating results of the above-described test. According to the results, the calculated error is within ±2.24 mm. However, as shown in FIG. 2B, the error within ±2.24 mm does not significantly affect the measurement results of the pulse waveform signals. Accordingly, only with the ratio, for example, I1/L1, of the width of the wrist to the distance between the left side end of the left wrist and the radial artery, and the width of the wrist of the user, the location of the radial artery from the left side end of the left wrist of the user may be estimated.

The mean of the width of the wrist and the ratio thereof, for example, I1/L2, of the distance between the left side end of the left wrist and the radial artery may be calculated by using the experimentally acquired result value as the constant. Accordingly, when measuring only the width of the wrist of the user, the location of the radial artery may be more accurately estimated irrespective of the user's sex, age, weight, and the like.

Referring again to FIG. 1, the information control unit 140 may calculate the displacement of the radial artery by multiplying the calculated distance between the first side portion 163 and the second side portion 164, which is the width of the wrist 161, and the constant which is calculated according to the test results described with FIGS. 2 through 4. As described above, the displacement of the radial artery may be set as the distance from the first side portion 163, corresponding to the left side end of the wrist 161, to the radial artery.

The sensor unit 151 is provided in the bracelet membrane 110, and measures the user's biosignal from the radial artery 162.

The sensor actuator 152 connects with the sensor unit 151, and moves the sensor unit 151. In this case, the sensor actuator 152 may include a motor, and the like, to move the sensor unit 151. Also, a predetermined rail unit may be installed in the bracelet membrane 110 to move the sensor unit 151 of the sensor actuator 152.

The information control unit 140 actuates the sensor actuator 152 by using the calculated displacement of the radial artery 162, and moves the sensor unit 151 towards the location of the radial artery 162. In this state, the information control unit 140 may measure the user's biosignal using the sensor unit 151.

The sensor unit 151 may include at least one sensor portion, which will be described in detail with reference to FIG. 5.

Figure 5:
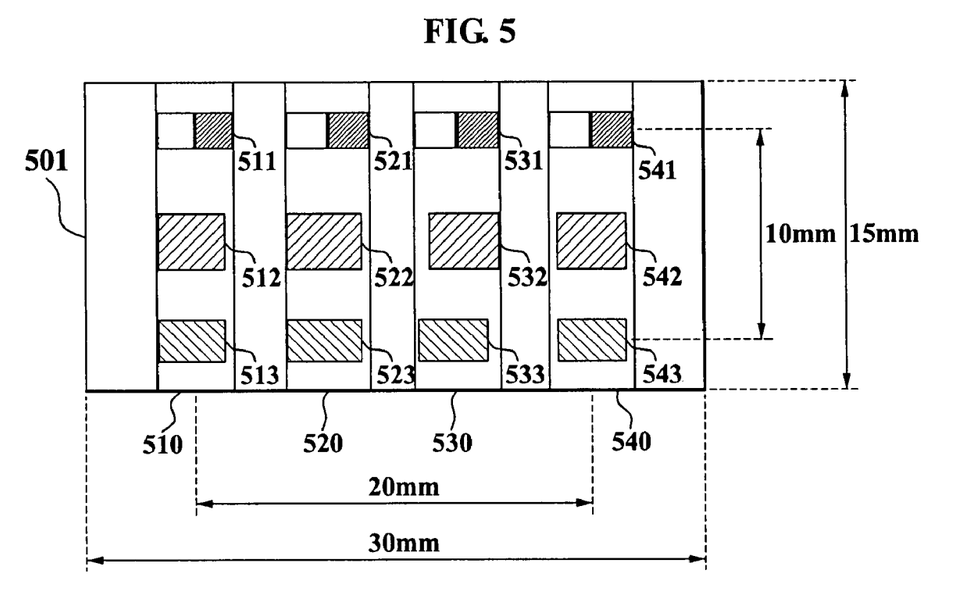
FIG. 5 is a diagram illustrating a structure of a sensor unit according to an exemplary embodiment of the present invention.

FIG. 5 is a diagram illustrating a structure of a sensor unit 501 according to an exemplary embodiment of the present invention.

As shown in FIG. 5, the sensor unit 501 according to the present exemplary embodiment may include four sensors, i.e. a first sensor portion 510, a second sensor portion 520, a third sensor portion 530, and a fourth sensor portion 540. Also, each of the sensor portions 510, 520, 530, and 540 may include one optical sensor 513, 523, 533, or 543, one pressure sensor 512, 522, 532, or 542, and four luminous elements 511, 521, 531, or 541.

Each of the optical sensors 513, 523, 533, and 543 may measure the user's pulse waveform from the radial artery. Each of the pressure sensors 512, 522, 523, and 542 may measure the user's blood pressure by measuring a pressure of the radial artery. Also, each of four luminous elements, which has two light sources, 511, 521, 531, and 541 may measure an oxygen saturation level according to a light absorption difference between the user's oxyhemoglobin and reduced hemoglobin, by using wavelengths of a red light band and an infrared ray band respectively.

As shown in FIG. 5, the sensor unit 501 according to the present exemplary embodiment may be designed to be about 30 mm in width and about 15 mm in length. Also, a distance between the first sensor portion 510 and the fourth sensor portion 540 may be designed to be about 20 mm. A distance between the luminous elements 511, 521, 531, and 541 and the corresponding optical sensors 513, 523, 533, and 543 may be designed to be about 10 mm. As described above, an error according to a change in the location of the radial artery for each user may be reduced by installing at least one sensor portion to the sensor unit 501, and thereby, enlarging an area from which to measure the radial artery.

Also, as described above, the user's pulse waveform, the user's blood pressure, and also the user's various biosignals, such as an oxygen saturation level, and the like, may be measured simultaneously by installing an optical sensor, a pressure sensor, and luminous elements in a single sensor portion.

According to the above-described embodiments of the present invention, there is provided a biosignal measurement device which enables a user to easily and readily measure the user's biosignals irrespective of the user's physical characteristics by accurately tracing a location of a radial artery of the user's wrist according to a value which is obtained by multiplying a width of the wrist and a predetermined constant, and measuring the user's biosignals from the radial artery.

Also, according to the above-described embodiments of the present invention, there is provided a biosignal measurement device which can measure a user's pulse waveforms by including at least one optical sensor, at least each luminous element to emit a red light and an infrared ray using the two light sources respectively, and at least one pressure sensor with respect to a sensor unit to measure the user's biosignals from a radial artery, and also can measure an oxygen saturation level according to a light absorption difference between the user's oxyhemoglobin and reduced hemoglobin, and can measure a pressure of the radial artery using the pressure sensor, and thereby enables the user to measure the user's blood pressure.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A biosignal measurement apparatus comprising:
a bracelet membrane configured to be worn around a user's wrist;
a fixing supporter installed in a first side portion of the bracelet membrane and configured to support a first side portion of the wrist;
a moving supporter installed in a second side portion of the bracelet membrane, configured to move towards the fixing supporter and closely attach to a second side portion of the wrist;
a sensor unit installed in the bracelet membrane and measuring the user's biosignal from a radial artery; and
an information control unit to calculate a distance between the first side portion of the wrist and the second side portion of the wrist by detecting a movement distance of the moving supporter, and to calculate a displacement of the radial artery of the wrist by using a predetermined constant and the calculated distance between the first side portion of the wrist and the second side portion of the wrist.

2. The apparatus of claim 1, wherein the predetermined constant is set as a value between 0.1 and 0.2.

3. The apparatus of claim 1, wherein the moving supporter comprises a predetermined elastic element, and the moving supporter closely attaches to the second side portion of the wrist according to an elastic motion of the elastic element.

4. The apparatus of claim 1, wherein the information control unit calculates the distance between the first side portion of the wrist and the second side portion of the wrist by using both a distance between the fixing supporter and the moving supporter before the elastic motion of the elastic element is performed, and a displacement of the elastic element according to the elastic motion.

5. The apparatus of claim 1, wherein the moving supporter comprises a predetermined bolt element, and closely attaches to the second side portion of the wrist according to a rotational motion of the bolt element.

6. The apparatus of claim 5, wherein the information control unit calculates the distance between the first side portion of the wrist and the second side portion of the wrist by using both a distance between the fixing support and the moving support before the rotational motion of the bolt element is performed, and a number of rotations of the bolt element according to the rotational motion.

7. A biosignal measurement apparatus comprising:
a bracelet membrane configured to be worn around a user's wrist;
a fixing supporter installed in a first side portion of the bracelet membrane and configured to support a first side portion of the wrist;
a moving supporter installed in a second side portion of the bracelet membrane, configured to move towards the fixing supporter and closely attach to a second side portion of the wrist;
an information control unit to calculate a distance between the first side portion of the wrist and the second side portion of the wrist by detecting a movement distance of the moving supporter, and to calculate a displacement of a radial artery of the wrist by using a predetermined constant and the calculated distance between the first side portion of the wrist and the second side portion of the wrist;
and a sensor unit installed in the bracelet membrane and measuring the user's biosignal from the radial artery,
wherein the information control unit calculates the displacement of the radial artery of the wrist by multiplying the constant and the calculated distance between the first side portion of the wrist and the second side portion of the wrist.

8. The apparatus of claim 1, wherein the displacement of the radial artery corresponds to a distance from the first side portion of the wrist to the location of the radial artery.

9. The apparatus of claim 1, further comprising: a sensor actuator connected with the sensor unit and moving the sensor unit, wherein the information control unit actuates the sensor actuator by using the calculated displacement of the radial artery of the wrist, and moves the sensor unit towards the location of the radial artery.

10. A biosignal measurement apparatus comprising:
a bracelet membrane configured to be worn around a user's wrist;
a fixing supporter to installed in a first side portion of the bracelet membrane and configured to support a first side portion of the wrist;
a moving supporter installed in a second side portion of the bracelet membrane, configured to move towards the fixing supporter, and closely attach to a second side portion of the wrist;
an information control unit to calculate a distance between the first side portion of the wrist and the second side portion of the wrist by detecting a movement distance of the moving supporter, and to calculate a displacement of a radial artery of the wrist by using a predetermined constant and the calculated distance between the first side portion of the wrist and the second side portion of the wrist;
a sensor unit installed in the bracelet membrane and measuring the user's biosignal from the radial artery; and
a sensor actuator connected with the sensor unit and moving the sensor unit, wherein the information control unit actuates the sensor actuator by using the calculated displacement of the radial artery of the wrist, and moves the sensor unit towards the location of the radial artery, and
wherein the sensor unit comprises four sensor portions, wherein each sensor portions comprises:
a pulse waveform sensor to measure the user's pulse waveform from the radial artery;
a luminous part to emit light toward the wrist respectively, and to measure an oxygen saturation level; and
a pressure sensor to measure the user's blood pressure by measuring a pressure of the radial artery.

11. The apparatus of claim 9, wherein the sensor unit comprises:
a pulse waveform sensor to measure the user's pulse waveform from the radial artery.

12. The apparatus of claim 11, wherein the sensor unit comprises:
a luminous part to emit light toward the wrist respectively, and to measure an oxygen saturation level.

13. The apparatus of claim 11, wherein the sensor unit comprises:
a pressure sensor to measure the user's blood pressure by measuring a pressure of the radial artery.

14. The apparatus of claim 12, wherein the luminous part comprises at least two light sources to emit a red light and an infrared ray towards the wrist respectively.

15. The apparatus of claim 3, wherein the elastic element is a spring.

16. The apparatus of claim 9, wherein the sensor actuator comprises a motor to move the sensor unit.

* * * * *

UNITED STATES PATENT AND TRADEMARK OFFICE
CERTIFICATE OF CORRECTION

PATENT NO. : 8,301,215 B2
APPLICATION NO. : 11/819923
DATED : October 30, 2012
INVENTOR(S) : Jong Youn Lee et al.

Page 1 of 1

It is certified that error appears in the above-identified patent and that said Letters Patent is hereby corrected as shown below:

In the Claims:

Column 9, Line 38, In Claim 10, after "supporter" delete "to".
Column 9, Line 43, In Claim 10, delete "supporter," and insert -- supporter --, therefor.

Signed and Sealed this
Seventh Day of May, 2013

Teresa Stanek Rea
*Acting Director of the United States Patent and Trademark Office*